United States Patent [19]
Hancock et al.

[11] 4,095,474
[45] Jun. 20, 1978

[54] MONITORING SYSTEMS AND INSTRUMENTS

[75] Inventors: Peter Hancock; Terence Edward Clifton, both of Bedford, England

[73] Assignee: Imperial Chemical Industries Limited, London, England

[21] Appl. No.: 706,553

[22] Filed: Jul. 19, 1976

[51] Int. Cl.² .................. G01M 7/00; G01N 17/00
[52] U.S. Cl. ............................................ 73/579; 73/86
[58] Field of Search ............... 73/67.2, 86, 32 A, 67.1, 73/679

[56] References Cited
U.S. PATENT DOCUMENTS

| | | | |
|---|---|---|---|
| 2,960,862 | 11/1960 | Spurr et al. | 73/67.2 |
| 3,240,054 | 3/1966 | Roth | 73/672 X |
| 3,253,219 | 5/1966 | Littler | 73/67.1 X |
| 3,420,092 | 1/1969 | Dorsch | 73/32 A |
| 3,610,027 | 10/1971 | Woboditsch | 73/67.2 |
| 3,808,875 | 5/1974 | Miller | 73/32 A |

Primary Examiner—James J. Gill
Attorney, Agent, or Firm—Cushman, Darby & Cushman

[57] ABSTRACT

Apparatus for monitoring parameters within an environment which is not readily accessible, for example for monitoring corrosion or deposition within industrial plant, comprises a vibratory element which is resiliently mounted in said environment and vibrated from outside said environment. The apparatus may be used by monitoring the resonant frequency of the vibratory element.

6 Claims, 3 Drawing Figures

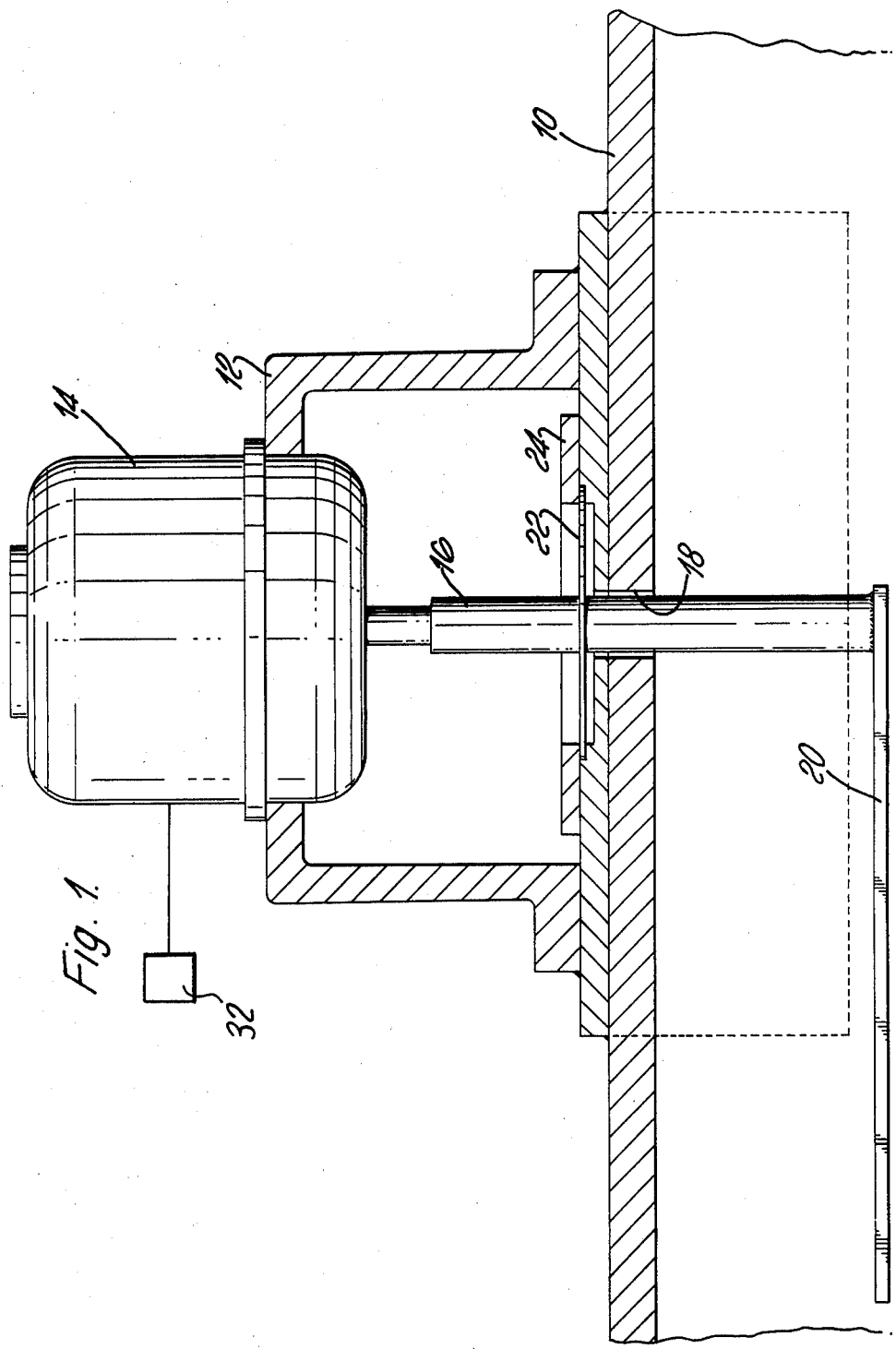

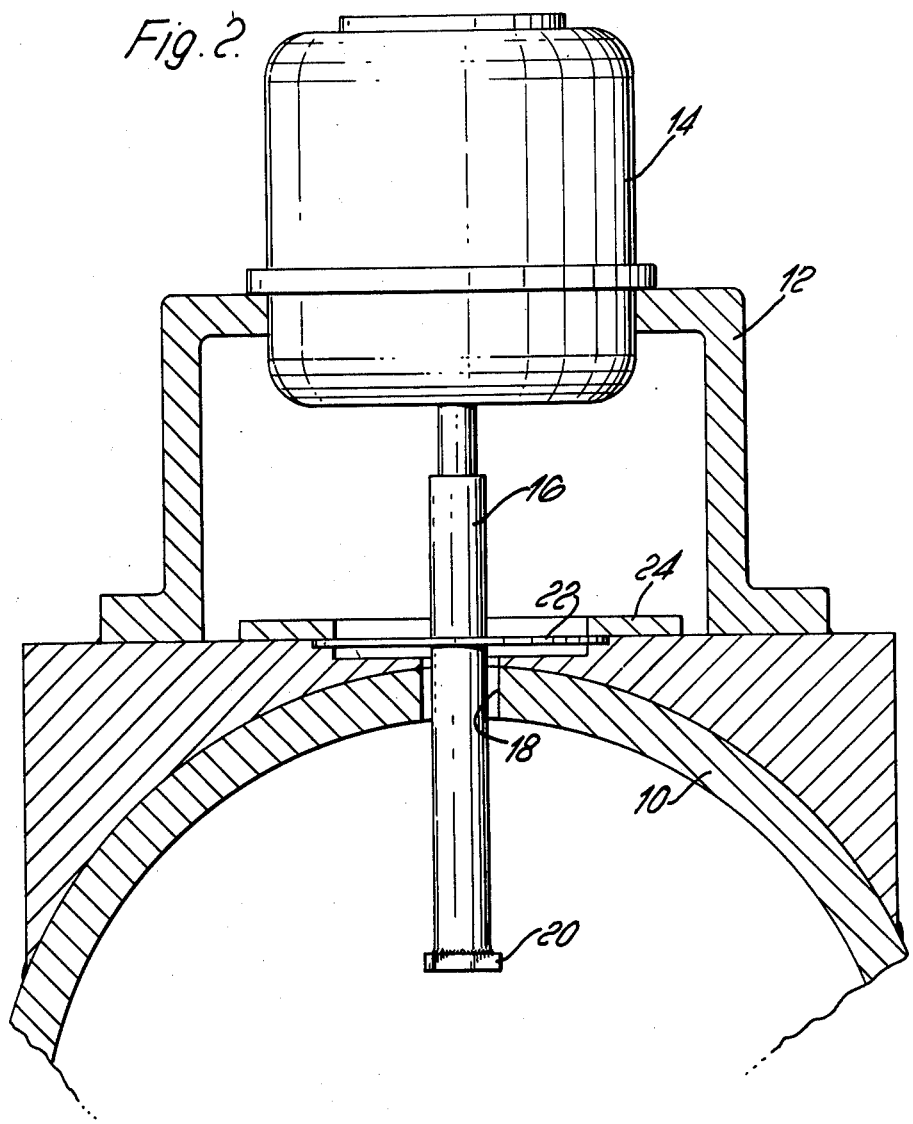

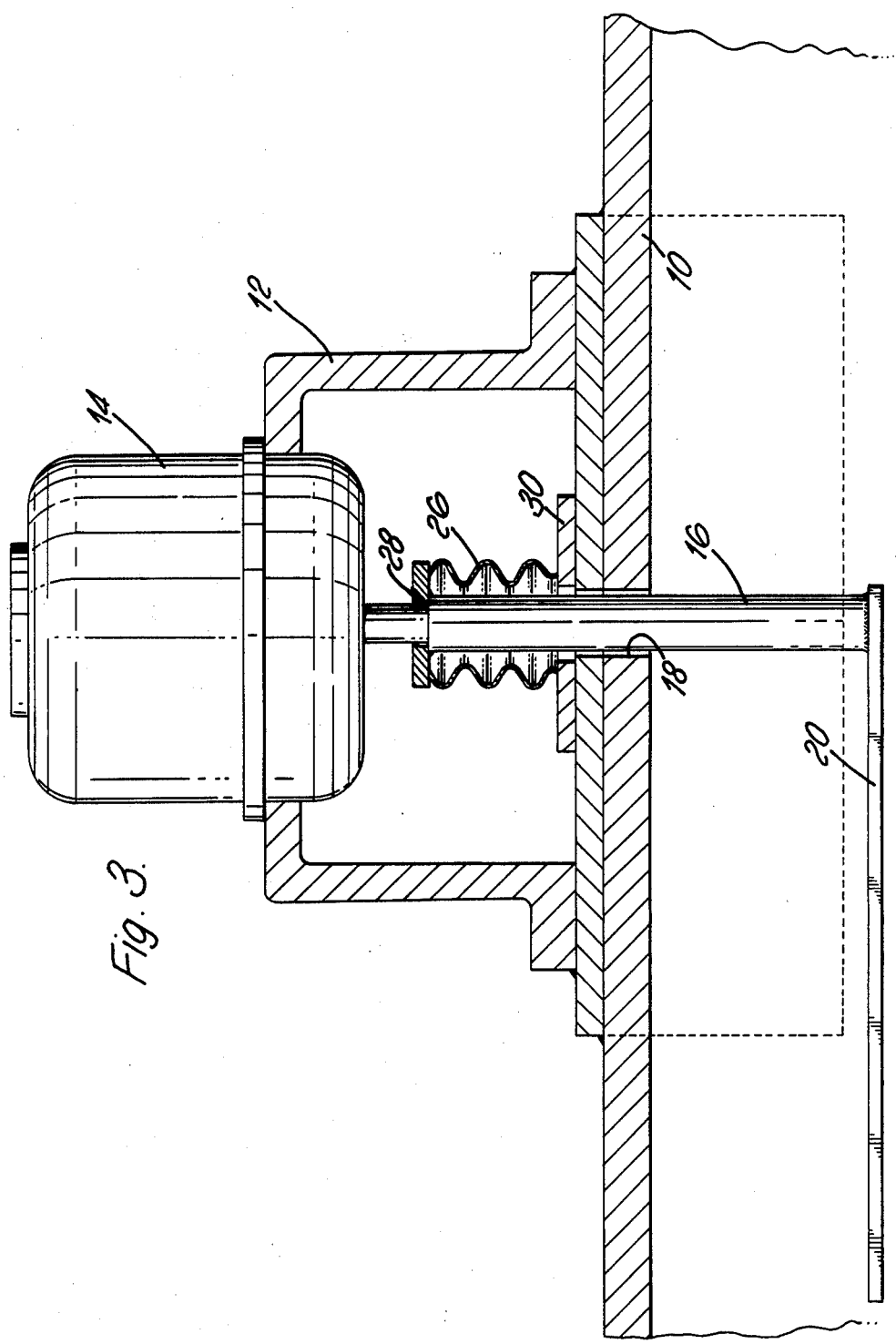

MONITORING SYSTEMS AND INSTRUMENTS

This invention relates to monitoring instruments and to methods of monitoring changing parameters within an environment which is not normally readily accessible.

In many branches of industry in particular, although the same or similar problems occur in other situations, it is extremely advantageous to be able to obtain on-line information concerning what is happening in an environment which is not readily accessible, for example inside a piece of industrial plant. For example, if one is concerned with furnaces, boilers, turbines, pipework or similar equipment, it is extremely helpful to be able to obtain information about the state of corrosion of the internal surfaces or about the rate of deposition of materials on the surfaces. Much industrial plant is operated in aggressive environments, for example at high or low temperatures, either because of the burning of solid, liquid or gaseous fuel or as a feature of a chemical process, or both. In furnaces and turbines for example, conventional equipment which is appropriate for the measurement of corrosion or surface deposition cannot survive at the elevated temperatures which are encountered or is not sufficiently sensitive to provide sufficiently meaningful results. Sensitivity is an important feature when one considers that the shutting down of a furnace, for example as a result of excessive corrosion, is an extremely expensive matter in terms of lost production, and accurate monitoring equipment is extremely beneficial if one can thereby run the plant for the maximum length of time before having to initiate shut-down. In the past, because of the lack of sensitive monitoring equipment, it has generally been necessary to build in considerable operational safety margins, that is to shut down the plant more frequently than conditions inside the plane require, with a consequent loss of efficiency.

In other situations it may be desired to monitor deposition or corrosion in very low-temperature conditions or in conditions where the monitoring device is exposed to potentially destructive atmospheric conditions, for example high wind-speeds. Such low-temperature conditions may be encountered in manufacturing processes (for example in crystallisation vessels) or in monitoring ice deposition for example on aircraft. In such situations there is a need for a robust device such as has not heretofore been available.

It is a primary object of the present invention to provide apparatus for and a method of monitoring an environment to provide information as to the state of corrosion or surface deposition occurring within that environment.

An important aspect of the invention is that no delicate detection equipment is used inside the environment being monitored and it is therefore capable of operating in extremely severe environments. Among the advantages of the apparatus of the present invention are that it can be fitted to any piece of industrial equipment or plant relatively easily, it is capable of operating at elevated or low temperatures, at high pressures, in situations where there is a high rate of flow of gas or liquid, and in atmospheres where deposition of chemical species or corrosion of equipment is likely to take place. It is suitable for use with a wide range of industrial equipment, and is capable of giving a continuous assessment of the state of deposition or corrosion inside any reaction vessel or chamber. Further, although it has been particularly developed for high temperature gaseous applications it is also suitable for measuring deposition or corrosion in liquids when chemical attack might be expected or where solid deposition from the liquid may occur. It is particularly applicable in situations where the density of the solid deposit is not close to that of the liquid; for example, it is of value in monitoring deposition in hot water systems.

The present invention is based upon monitoring the resonant frequency of a vibrated element and using this information as a means of measuring for example deposition and/or corrosion, in that the resonant frequency of a vibrated element will change as corrosion occurs or as materials are deposited on it.

Broadly in accordance with one aspect of the present invention there is provided apparatus for monitoring parameters within an environment, comprising a vibratory element arranged to be positioned within said environment, means to couple said element to a point beyond a wall delimiting said environment and to transmit vibrations to the element when vibrated at said point, and resilient support means arranged to be disposed between said coupling means and said wall, the resonant frequency of the vibratory element being different from that of the coupling means and that of the support means.

The environment to be monitored may, for example, be that within a chamber, in which case the coupling means extends through a wall of said chamber. Alternatively, the environment may be an external environment monitored from within an aircraft, container or building, in which case the wall is that of said aircraft or the like.

The vibratory element may advantageously be elongated, although elements of other shapes may be used. For example, the element may be in the form of a hoop of material of rectangular cross-section, or a disc. When an elongated element is used it may usefully be supported by the coupling means at or adjacent to one of the ends of the element. The coupling means may comprise a bar, which may be in the form of an elongated rod, or a tube and it may be arranged to have a vibrator connected to it at its end remote from the element. In another form, the coupling means may comprise two components, adapted to be disposed on opposite sides of the wall of the chamber and linked together magnetically. The components may be separated by the wall of the chamber adjacent a narrowing of the chamber wall or the support means, for example in the form of a diaphragm, may be disposed between the components. In another form, the coupling means may be a magnetostrictive device, in which a magnetic field generated at a point on one side of the wall causes a component on the other side of the wall to vibrate.

The resilient support means may take a variety of forms. As already envisiaged, the support means may be a diaphragm, for example of stainless steel. Another advantageous arrangement is for the support to be in the form of a bellows. According to yet another feature of the invention, the support means may be channel or bore in the wall of the chamber, within which a coupling means in the form of a bar or tube may be a close sliding fit. Especially when the coupling means is elongated, it may be desired to provide resilient support, for example a resilient spider, additional to that afforded by the resilient support means and optionally unconnected with the latter.

Also in accordance with the present invention there is provided a method of monitoring parameters within an environment, comprising supporting within said environment a vibratory element, transmitting to said element via resiliently-supported coupling means, vibrations applied to said coupling means at a point lying outside said environment and monitoring signals indicative of the resonance of the vibratory element to detect changes in said parameters. Thus if, for example, the coupling means is vibrated by means of an electrically-powered vibrator, then resonance of the element may be detected using detector means to determine when the power supply to the vibrating means is at a minimum value. If the voltage of the supply is maintained at a fixed value, then resonance may be detected as the point of minimum current flow to the vibrator.

Compensation may be provided for temperature changes which affect the resonant frequency of the vibratory element, for example by the use of thermocouples or other temperature-measuring devices fitted into the vibratory element or the coupling means; preferably the device is fitted to the vibratory element itself. Alternatively, the need for such compensation may be avoided by the use of a vibratory element comprising at least two different metals, so related that the resonant frequency of the element is substantially independent of temperature.

The frequency of the vibrations applied to the coupling means will of course be related to the resonant frequency of the vibratory element; the dimensions of the element will therefore be chosen bearing in mind the desirable or available range of vibrator frequencies. In general, the frequency of the input vibrations will normally lie within the range from 0.01 to 10 KHz and preferably within the range from 0.3 to 3 KHz. It is desirable to avoid frequencies which are strong harmonics of the frequency of the power supply to the vibrator.

Apparatus in accordance with the present invention will now be briefly described by way of example and with reference to the accompanying drawings, in which:

FIG. 1 is a part-sectional side view of one embodiment of the invention, as viewed perpendicular to the longitudinal axis of a cylindrical chamber within which the monitor is located;

FIG. 2 is a part-sectional end view of the apparatus in FIG. 1, viewed along the longitudinal axis of the chambers; and FIG. 3 is a part-sectional side view in a direction corresponding to that of FIG. 1, of an alternative embodiment of the present invention.

Referring to FIGS. 1 and 2 of the drawings, these show part of the wall 10 of a closed reaction vessel or chamber, which in the present illustration is circular in cross-section. The monitoring unit of the present invention is mounted on the outside of the chamber wall and comprises a housing 12 which can be welded, screwed or otherwise secured to the chamber wall. Secured in the housing 12 is an electromechanical vibrator 14 and from this there extends towards the chamber wall a coupling rod 16 which may be a solid rod or a hollow tube. The coupling rod 16 passes through a hole 18 in the chamber wall 10 of a size slightly larger than the cross-section of the rod. At the end of the coupling rod 16 within the chamber there is secured a reed 20 which is supported at one end as a simple cantilever. The reed 20 may for example be welded to the rod 16. The attitude and position of the reed 20 within the chamber will depend upon the particular operating conditions and the direction of any flow within the chamber. The coupling rod 16 is supported adjacent to the chamber wall 10 by a diaphragm 22 which is fixed into the wall by a clamping plate 24. The diaphragm 22 may be for example a circular disc suitably apertured at its centre to provide secure mechanical engagement with the rod 16, and additionally it may be welded to the rod.

The sizes and materials selected for the rod 16, the reed 20 and the diaphragm 22 will depend upon the particular working environment in which they are to be used. For many applications however stainless steel is an appropriate material for these components. It is an important feature of the present invention that the resonant frequency of the reed 20 must be different from that of the rod 16 and of the diaphragm 22 in order that the output signals representative of the resonant frequency of the reed shall not be masked or made ambiguous by signals from the rod 16 or from the diaphragm 22.

In use, the vibrator 14 is energised from an external electrical source (not shown) and vibrations, for example of the order of 1 KHz, are transmitted to the reed 20. By appropriate arrangements, pressure can be equalised on the two sides of the diaphragm 22 to enable it to operate in an unstrained condition. This may be achieved, for example, by providing a link between the contents of the chamber and the interior of the housing 12. Alternatively, an independent supply of, say, an inert gas, for example nitrogen, may be provided to the interior of the housing 12, an equalising controller being employed to maintain the pressure in the housing 12 in balance with that in the reaction chamber.

Provision may be made, when appropriate, for cooling the diaphragm 22 to maintain it at an acceptable operating temperature below that obtaining in the reaction chamber. For example, a supply of cooling air or inert gas may be employed.

As corrosion occurs in the material of the reed 20 or as materials are deposited on its surface, its resonant frequency changes. The resonant frequency of the reed 20 is affected by four factors, namely its mass, its modulus of elasticity, its dimensions and its temperature. Compensation for temperature variations can be provided and it is essentially the change in resonant frequency due to changes in the mass, modulus or dimensions of the reed 20 which is detected in accordance with the present invention.

In order to compensate for temperature fluctuations which will produce changes in the resonant frequency of the reed 20, thermocouples (not shown) may be fixed into the reed or into the coupling rod 16, particularly if this is hollow, and output signals from the thermocouples can be used to provide signals representative of temperature changes and of such magnitude as to off-set the change in resonant frequency signal attributable to temperature effect alone.

Appropriate electrical control apparatus is used with the monitor. The resonance of the reed is detected by monitoring the input current to the vibrator 14. At resonance the input current is at a minimum and, as with any high Q mechanical system, detection of very small resonant frequency changes is possible detector means for determining when the power supply to the vibrator is at a minimum value is shown generally at 32 in FIG. 1. The sensitivity of the apparatus is therefore extremely high and very small changes in the mass, modulus or dimensions of the reed 20 can be detected. Using a bridge method, the small changes in the input current to the vibrator 14 are amplified and displayed, for example on a meter. The resonant frequency can then be recorded at the minimum current trough. Prior calibration of resonant frequency against temperature is preferably carried out and appropriate corections made for temperature changes, either by calculation or by direct electrical off-setting as described above.

FIG. 3 of the drawings illustrates an alternative embodiment, broadly similar to that of FIGS. 1 and 2 but in which the resilient support means for the coupling rod 16 takes the form of a stainless steel bellows 26, secured at 28 to the coupling rod and by means of a plate 30 to the chamber wall 10.

While, by prior calibration, the apparatus of the present invention may be used to determine resonant frequency as such, it will more usually be used to monitor either changes in resonant frequency or changes in the rate of change. Thus, when the apparatus is employed to monitor corrosion or deposition, a predetermined rate of corrosion or deposition may be acceptable but changes in that rate, more particularly acceleration of the rate, may indicate a significant change in plant or process conditions meriting attention. A marked change in the resonant frequency may indicate embrittlement of the reed giving rise to a change in its modulus of elasticity. Since, in many situations, the material of the reed will be chosen to match the material of potentially vulnerable plant items, in such sitatutions corrosion or embrittlement of the reed will be a direct indication of similar damage, or potential damage, to the plant.

The apparatus of the present invention can be built into a fully automatic system to monitor changes in corrosion or surface deposition on the reed. In a fully automatic system, the resonant frequency can be detected by using phase angle detectors, since the phase angle between the vibrator current and the vibrator voltage moves towards zero as the reed specimen is tuned. An electronic servo-system can be used to tune the system continuously and automatically and record frequency changes, for example on a strip chart recorder or digital recorder. A loop in the servo-system can be provided to correct automatically for the unwanted frequency changes due to temperature fluctuations all of such means are represented diagrammatically in the drawings (FIG. 1) at 32.

Although the foregoing description has referred to the monitoring apparatus as being particularly useful in monitoring corrosion and rate of deposition of materials in industrial plant, the basic system is capable of much wider application. For example, the monitoring unit can be used to detect the depositing of scale in industrial hot water systems. It would be relatively simple to provide the basic part of the monitoring unit, i.e. the reed, coupling rod and diaphragm, in an appropriate part of a plurality of hot water systems and the rate of deposition of scale in the individual hot water systems could then be checked at intervals by using a portable vibrator and electronic system which could be coupled to the individual monitor units.

We claim:

1. Monitoring apparatus utilizable with a wall delimiting at least in part an environment to be monitored, and comprising means for continuously monitoring a continuously changing environmental condition in the environment said means comprising:
   an elongated vibratory element, said continuously monitoring means comprises means for detecting the amount of corrosion or surface deposition on the vibratory element,
   vibration originating means located exterior of said environment,
   coupling means affixed to said element for operatively coupling said vibratory element to said vibration originating means and for transmitting vibrations from said vibration originating means to said vibratory element,
   means for resiliently supporting said coupling means relative to said wall so that said vibratory element is disposed within said environment, and
   the resonant frequency of said vibratory element being different from the resonant frequency of said coupling means or said supporting means.

2. Apparatus according to claim 1, in which the coupling means is a bar or tube passing through the wall and connected thereto by said support means.

3. Apparatus according to claim 2, in which the support means is a diaphragm.

4. Apparatus according to claim 2, in which the support means is a bellows.

5. A method of continuously monitoring a continuously changing environmental condition in an environment, comprising the steps of
   supporting a vibratory element within the environment to be monitored,
   transmitting to the vibratory element through resiliently supported coupling means vibrations applied to said coupling means from a point exterior of the environment, and
   monitoring signals indicative of the resonance of the vibratory element to thereby detect changes in the amount of corrosion or surface deposition on the vibratory element responsive to exposure of the element to the environment to be monitored.

6. A method as recited in claim 5 wherein said step of transmitting vibrations to said vibratory element is accomplished by supplying power to a vibrator associated therewith and external of the environment, and wherein said step of monitoring signals indicative of the resonance of the vibratory element is accomplished by monitoring the power flow to said vibrator and determining when it is at a minimum.

* * * * *